(12) United States Patent
Nakajima et al.

(10) Patent No.: US 10,080,556 B2
(45) Date of Patent: Sep. 25, 2018

(54) RETRACTOR

(71) Applicants: TOKUSEN KOGYO CO., LTD., Hyogo (JP); OSAKA UNIVERSITY, Osaka (JP)

(72) Inventors: Kiyokazu Nakajima, Osaka (JP); Hiroyuki Yamashita, Hyogo (JP)

(73) Assignees: TOKUSEN KOGYO CO., LTD., Hyogo (JP); OSAKA UNIVERSITY, Osaka (JP)

( * ) Notice: Subject to any disclaimer, the term of this patent is extended or adjusted under 35 U.S.C. 154(b) by 190 days.

(21) Appl. No.: 15/038,882

(22) PCT Filed: Mar. 28, 2014

(86) PCT No.: PCT/JP2014/059262
§ 371 (c)(1),
(2) Date: May 24, 2016

(87) PCT Pub. No.: WO2015/079719
PCT Pub. Date: Jun. 4, 2015

(65) Prior Publication Data
US 2017/0000472 A1  Jan. 5, 2017

(30) Foreign Application Priority Data
Nov. 26, 2013  (JP) ................................. 2013-243891

(51) Int. Cl.
*A61B 17/02* (2006.01)
*A61B 17/00* (2006.01)

(52) U.S. Cl.
CPC .... *A61B 17/0218* (2013.01); *A61B 17/00234* (2013.01); *A61B 17/02* (2013.01);
(Continued)

(58) Field of Classification Search
CPC ................................................. A61B 17/0218
See application file for complete search history.

(56) References Cited

U.S. PATENT DOCUMENTS 5,275,610 A * 1/1994 Eberbach ............... A61M 29/02
604/105
6,423,080 B1  7/2002 Gellman et al.
(Continued)

FOREIGN PATENT DOCUMENTS

EP  2260772 A1  12/2010
JP  06-154152 A  6/1994
(Continued)

OTHER PUBLICATIONS

Extended European Search Report in EP Application No. 14865996.4 dated Aug. 3, 2017, 6 pages.
(Continued)

*Primary Examiner* — Christian Sevilla
(74) *Attorney, Agent, or Firm* — Marshall, Gerstein & Borun LLP (57) ABSTRACT

A retractor has a rigid piercing tube and an expansion body. The expansion body has an introduction tube which is received within the piercing tube, a movable wire which is received within the introduction tube, and stationary wires which are arranged around the movable wire. The proximal end of each of the stationary wires is affixed to the distal end of the introduction tube. The distal end of each of the stationary wires is joined to the distal end of the movable wire. The respective proximal ends of the piercing tube, the introduction tube, and the movable wire are respectively joined to first, second, and third grip sections.

4 Claims, 7 Drawing Sheets

(52) U.S. Cl.
CPC ............... *A61B 2017/0042* (2013.01); *A61B 2017/00349* (2013.01)

(56) References Cited

U.S. PATENT DOCUMENTS

| | | |
|---|---|---|
| 2004/0236186 A1 | 11/2004 | Chu |
| 2007/0005093 A1 | 1/2007 | Cox |
| 2011/0160538 A1* | 6/2011 | Ravikumar ...... A61B 17/00234 600/204 |
| 2011/0224494 A1 | 9/2011 | Piskun et al. |
| 2013/0144118 A1 | 6/2013 | Piskun et al. |
| 2013/0231534 A1 | 9/2013 | Piskun et al. |
| 2013/0324795 A1 | 12/2013 | Nakajima et al. |
| 2015/0223798 A1 | 8/2015 | Piskun et al. |
| 2015/0265818 A1 | 9/2015 | Piskun et al. |
| 2015/0313584 A1 | 11/2015 | Piskun et al. |
| 2015/0335324 A1 | 11/2015 | Piskun et al. |
| 2016/0015252 A1 | 1/2016 | Piskun et al. |
| 2016/0309996 A1 | 10/2016 | Piskun et al. |
| 2017/0196549 A1 | 7/2017 | Piskun et al. |

FOREIGN PATENT DOCUMENTS

| | | |
|---|---|---|
| KR | 10-2013-0009742 A | 1/2013 |
| WO | WO-2012/114569 A1 | 8/2012 |

OTHER PUBLICATIONS

Decision of Refusal in JP Application No. 2015-550579 dated Oct. 17, 2017, 9 pages.
International Preliminary Report on Patentability and Written Opinion in International Application No. PCT/JP2014/059262 dated May 31, 2016, 7 pages.
Search Report in International Application No. PCT/JP2014/059262 dated May 13, 2014.

\* cited by examiner

RETRACTOR

CROSS-REFERENCE TO RELATED APPLICATION

This application is based upon and claims the benefit of the priority of prior Japanese Patent Application No. 2013-243891, filed on Nov. 26, 2013, the entire contents of which are incorporated herein by reference.

TECHNICAL FIELD

The present invention relates to retractors, and more specifically, to a retractor that can be developed in a three-dimensional direction to be used to exclude an inside wall of a hollow organ or an organ in a body cavity.

BACKGROUND ART

In a conventional laparotomy, the organ that inhibits the surgery can be manually spread, but it is known that the organ cannot be easily spread and that it is difficult to ensure a field of view optimum for the surgery under endoscopic surgery. For example, a method of injecting gas into the body cavity to ensure the field of view and the operation space is known, but such method requires full anesthesia and the invasiveness is not actually low.

To alleviate the problem of field of view, and the like and to facilitate the endoscopic treatment, an instrument called a retractor that excludes or tugs an organ to be treated or an organ that inhibits the field of view during the treatment, and the like, has been developed. As a basic function, it is desired that an instrument can be inserted through a small opening passage such as a trocar (pallium tube) or a small incision that serves as an insertion passage when inserting the retractor into the body. Therefore, the retractor needs to have a small diameter (e.g., desirably smaller than or equal to 10 mm in the case of trocar, and smaller than or equal to 20 mm in the case of small incision) and to have a rod-like form at least at the time of insertion, whereas after the insertion into the body cavity, the retractor is demanded to be deformable to a shape an excluding section has a large area of a certain degree to widely and safely exclude the target.

According to the conflicting demands described above, variously devised retractors are being proposed and are commercially available. For example, the retractor in which the excluding section opens to a fan shape has been provided (e.g., Patent Literature 1). At the time of insertion of the trocar into the abdominal cavity, a fan-shaped excluding section is folded and accommodated inside a rod-shaped tube, and is pushed out by the rod-shaped tube in the body cavity to be spread to a fan shape. A structure of opening the fan-shaped excluding section to an arbitrary size by manual operation and a structure in which an angle between the excluding section and a base section varies are known, where such structures are suited for excluding liver and intestine as the advantage thereof is that the organ can be excluded relatively widely. The shape is not limited to a fan shape, and various shapes such as a diamond shape, and the like have also been proposed.

In particular, development of a retractor that more effectively excludes the organ and that excels in operability is desired.

CITATION LIST

Patent Literature

Patent Literature 1: JP 6-154152 A

SUMMARY OF INVENTION

Technical Problem

The present invention aims to solve the problems described above, and the object thereof is to provide a retractor that can be inserted through an incision or by being directly perforated to exclude the inside wall of the hollow organ or the organ in the body cavity, the retractor being easy to handle in the surgery and being able to freely adjust the scale of exclusion.

Solution to Problem

The present invention is a retractor for excluding an inside wall of a hollow organ or an organ in a body cavity, and the retractor includes:
a rigid perforation tube;
a developing body that is configured to be accommodated and extended with respect to the perforation tube; and
a grip connected to respective proximal ends of the perforation tube and the developing body, wherein
the developing body includes
an excluding section configured by a movable wire and a plurality of fixing wires arranged at a periphery of the movable wire, and
an introducing tube extended from the excluding section, the movable wire being passed through the introducing tube; and
a distal end of the movable wire and a distal end of the fixing wire are joined in the excluding section.

In one embodiment, the grip includes a first grip portion, a second grip portion, and a third grip portion from a distal side;
a proximal end of the perforation tube is connected to the first grip portion;
a proximal end of the introducing tube of the excluding section is connected to the second grip portion; and
a proximal end of the movable wire of the excluding section is connected to the third grip portion.

In one embodiment, the perforation tube is a straight tube.

In one embodiment, a cross-section of the movable wire has a substantially circular shape.

In further embodiment, a cross-section of the fixing wire has a partial circular ring shape in which a part of the cross-section substantially coincides with one part of an outer periphery of the cross-section of the movable wire.

In one embodiment, a curve of the fixing wire in the excluding section is controlled by pushing or pulling at least one of the second grip portion or the third grip portion with respect to the first grip portion.

Advantageous Effects of Invention

According to the present invention, a retractor that can freely exclude the organ can be provided. The retractor of the present invention can form a cocoon-shaped structure configured to an arbitrary size in an excluding section by pushing and pulling a grip separated into three portions. The cocoon-shaped structure enables the organ to be freely excluded.

According to the present invention, the organ within a predetermined range can be excluded without injecting gas into the body cavity, and hence, a so-called gas-less surgery can be performed.

BRIEF DESCRIPTION OF DRAWINGS

FIGS. 2A to 2C are views showing the retractor of the present invention shown in FIG. 1, where

FIGS. 3A and 3B are views schematically showing one example of the developing body configuring the retractor of the present invention, where

FIGS. 7A to 7C are schematic cross-sectional views of the retractor showing one example of the retractor of the present invention, where

DESCRIPTION OF EMBODIMENTS

The present invention will be described in detail using the drawings.

Figure 1:
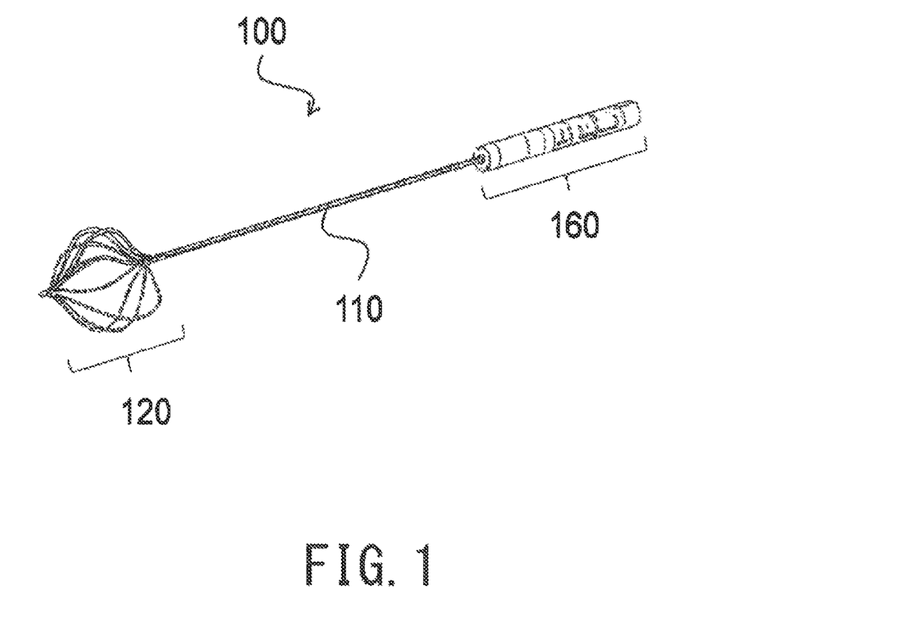
FIG. 1 is a view schematically showing one example of a retractor of the present invention, and is a perspective view of the retractor showing a state in which a developing body is opened.

FIG. 1 is a view schematically showing one example of a retractor of the present invention, and is a perspective view of the retractor showing a state in which a developing body is opened.

A retractor 100 of the present invention includes a rigid or hard perforation tube 110, a developing body 120 that can be accommodated and extended with respect to the perforation tube 110, and a grip 160 connected to a respective proximal end of the perforation tube 110 and the developing body 120.

Figure 2A:
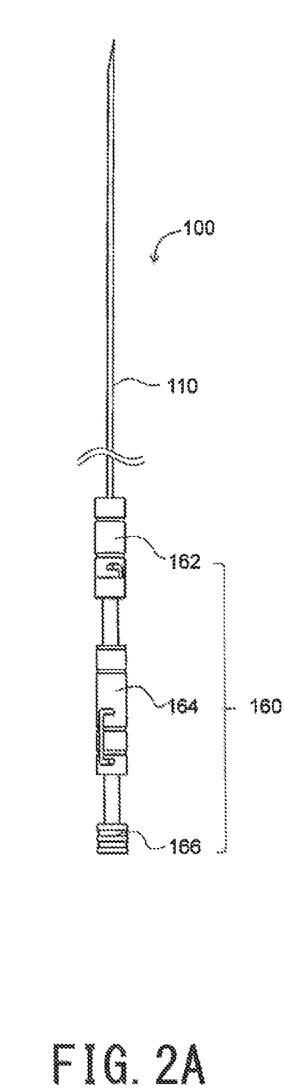
FIG. 2A is a schematic view of the retractor showing a state in which the developing body is accommodated in a perforation tube.

FIGS. 2A to 2C are side views of the retractor 100 of the present invention shown in FIG. 1. As shown in FIG. 2A, the retractor 100 of the present invention has, for example, the developing body completely accommodated in the perforation tube 110 immediately before use. The proximal end of the perforation tube 110 is connected to a first grip portion 162 of the grip 160.

The term "retractor" used in the present specification refers to a medical instrument for excluding, spreading, tugging, or elevating a target (e.g., organ) or anything that inhibits a field of view in a medical field, and for example, includes a trocar and a pallium tube. The operations of excluding, spreading, tugging, or elevating are sometimes collectively referred to as "retraction" or "retract". When simply referring to "exclusion" in the present specification, this may include not only the operation of exclusion but also operations of spreading, tugging, or elevating (i.e., refers to retraction). The retractor includes an excluding section, as will be hereinafter described, for example, and is required to have such excluding section deformable to a size of a certain extent after being inserted into the body.

The term "distal" used in the present specification refers to a position far from the person operating the retractor, and the term "proximal" refers to a position close to the person operating the retractor as opposed to the term "distal". Thus, the term "distal end" represents an end farthest (i.e., at distant) from the operating person, and the term "proximal end" represents an end closest (i.e., at proximate) to the operating person when operating the retractor of the present invention.

When referring again to FIG. 2A, in one embodiment, the perforation tube 110 is, for example, configured from a straight tube cut such that the distal end side has a sharp pointed shape. The angle of a tip of the distal end of the perforation tube 110 is not particularly limited, but is processed to an angle (e.g., 20° to 50°) at which the perforation into the body is facilitated. The outer diameter of the perforation tube 110 is preferably 1.7 mm to 3.5 mm, and more preferably 2.2 mm to 3 mm. Furthermore, the inner diameter of the perforation tube 110 can be selected from a range of preferably 1.5 mm to 3 mm, and more preferably 1.6 mm to 2.2 mm with respect to the outer diameter. In the present invention, the shape of the tip of the distal end of the perforation tube 110 is not necessarily limited to the description made above, and for example, may have an arbitrary shape that can be adopted to the pallium tube or the trocar in the medical field.

Such perforation tube 110 is preferably made from a rigid material, for example, metal such as stainless steel, tantalum, cobalt alloy, nitinol (nickel-titanium alloy), and the like. The stainless steel includes, for example, SUS304, SUS316, and SUS316L. The retractor 100 of the present invention can reliably perforate a desired position (e.g., abdominal cavity) without being concerned about deflection, bend, breakage, and the like of the perforation tube by using the perforation tube 110 made from such rigid material. Furthermore, as the perforation tube 110 is rigid, sufficient strength can be maintained even in the cocoon-shaped development in the excluding section, to be described later, and the retraction.

The grip 160 is divided into three portions, a first grip portion 162, a second grip portion 164, and a third grip portion 166 in the order from the distal end side. The type of material configuring the grip 160 is not particularly limited. The grip 160 is made, for example, from resin such as ABS resin, polycarbonate resin, acryl resin, and the like, metal such as stainless steel, aluminum, and the like, and the combination thereof.

Figure 2B:
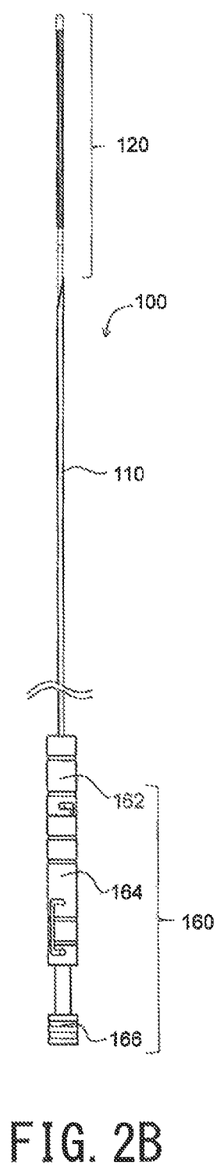
FIG. 2B is a schematic view of the retractor showing a state in which the developing body is extended from the perforation tube to carry out a cocoon-shaped development in an excluding section of the developing body.

FIG. 2B is a view schematically showing one example of the retractor 100 of the present invention, and is a schematic view of the retractor 100 showing a state in which the developing body 120 is extended from the perforation tube 110 to carry out the cocoon-shaped development in the excluding section of the developing body.

In the present specification, the term "cocoon shape" is a shape formed by the curve of a plurality of fixing wires, to be described later, in the excluding section of the developing body, and for example, includes a shape of a cocoon-like or oval sphere (rugby ball, etc.).

The retractor 100 of the present invention can take in and out the developing body 120 accommodated in the perforation tube 110 by pushing and pulling at least one of the second grip portion 164 and the third grip portion 166 in the grip 160 with respect to the first grip portion 162. The developing body 120 is designed to a size having an outer diameter of preferably 1.5 mm to 3 mm, and more preferably 1.6 mm to 2 mm, and so as to freely slide in the perforation tube 110 when accommodated in the perforation tube 110 (state in which development described later is not carried out). The entire length of the retractor of the present invention is not necessarily limited and, for example, a distance from the distal end to the proximal end of the perforation tube 110 (i.e., distance from distal end of the perforation tube 110 to distal end of the first grip portion 162) is preferably 100 mm to 300 mm.

Figure 2C:
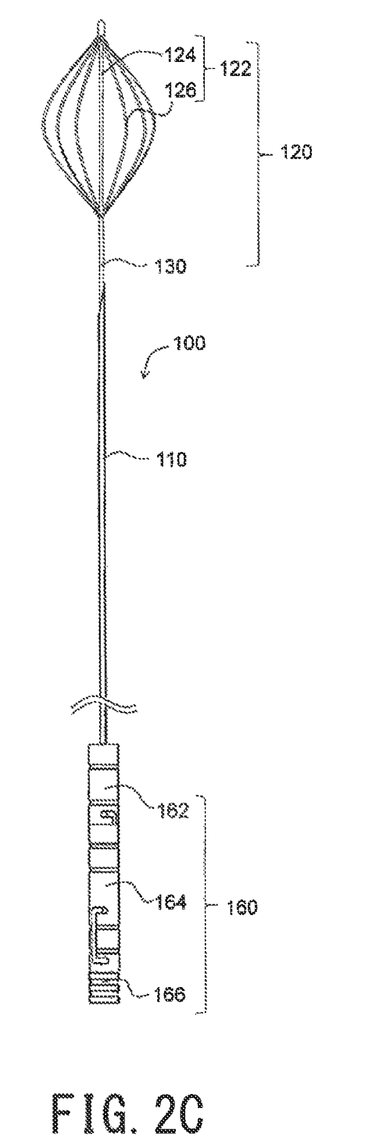
FIG. 2C is a schematic view of the retractor showing a state in which a cocoon-shaped structure is developed in the excluding section of the developing body extended from the perforation tube.

FIG. 2C is a view schematically showing one example of the retractor 100 of the present invention, and is a schematic view of the retractor 100 showing a state in which the cocoon-shaped structure is developed in the excluding section 122 of the developing body 120 extended from the perforation tube 110.

The retractor 100 of the present invention can develop the developing body 120 by further pushing and pulling at least one of the second grip portion 164 or the third grip portion 166 in the grip 160 with respect to the first grip portion 162. The developing body 120 includes the excluding section 122 and an introducing tube 130 extended from the excluding section 122, where the excluding section 122 is configured by a movable wire 124 and a plurality of fixing wires 126 arranged at the periphery of the movable wire 124. Moreover, the introducing tube 130 has a tubular shape, and the movable wire 124 is slidably passed therethrough. The number of fixing wires 126 arranged at the periphery of the movable wire 124 is not particularly limited, and is, for example three to twelve, and preferably six to eight.

An example of a material configuring the introducing tube 130, the movable wire 124, and the fixing wire 126 independently includes stainless steel such as SUS304, resin such as polyamide, PTFE, and the like, stainless steel on which resin is coated, and the like. In particular, the movable wire 124 preferably has a line strength sufficient to withstand load at the time of exclusion, for example, line strength of greater than or equal to 1850 MPa, and preferably greater than or equal to 2100 MPa.

The movable wire 124 and the fixing wire 126 configuring the excluding section 122, as well as, the introducing tube 130 preferably have a smooth surface to prevent damage on the organ. Furthermore, a coating material having electrical insulating property may be applied on such surfaces to prevent generation of sparks with another instrument during the surgery. The coating material may be a material normally used for coating of a medical instrument. For example, the coating material may be porous polytetrafluoroethylene (ePTFE) film, silicone film, polyurethane film, polyethylene terephthalate (Dacron (registered trademark)) film, and the like. The thickness of the coating layer formed by the coating material is not particularly limited, but is, for example, 4 μm to 16 μm, and preferably 8 μm to 12 μm.

The length of the excluding section 122 accommodated (undeveloped) in the perforation tube 110 fluctuates according to the size, and the like of the designed retractor, and hence is not necessarily limited. In one embodiment, the length of the excluding section accommodated in the perforation tube 110 is, for example, 40 mm to 120 mm, and preferably 50 mm to 80 mm. Moreover, in one embodiment, the size of the outer diameter of the excluding section 122 accommodated in the perforation tube 110 is, for example, 1.5 mm to 3 mm, and preferably 1.6 mm to 2 mm.

The length in the most developed state of the excluding section 122 and the maximum diameter of the cocoon shape formed when the fixing wire 126 of the excluding section 122 is developed fluctuate by the size of the designed retractor, and the like, and thus are not necessarily limited. In one embodiment, the length of the excluding section is, for example, 35 mm to 80 mm, and preferably, 45 mm to 65 mm. Furthermore, in one embodiment, the maximum diameter of the cocoon shape is, for example, 20 mm to 80 mm, and preferably, 35 mm to 60 mm.

Figure 3A:
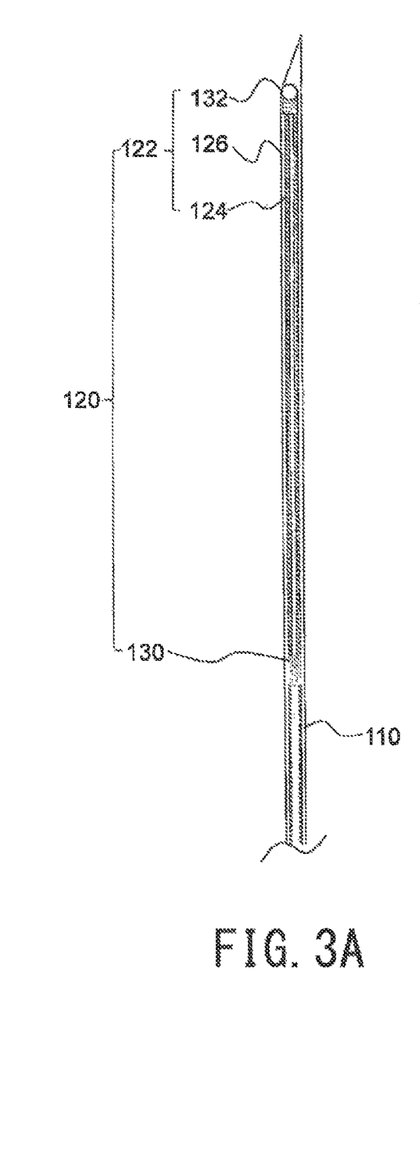
FIG. 3A is a cross-sectional view in a longitudinal direction of a distal end portion of the retractor of the present invention showing a state in which the developing body is accommodated in the perforation tube.
Figure 3B:
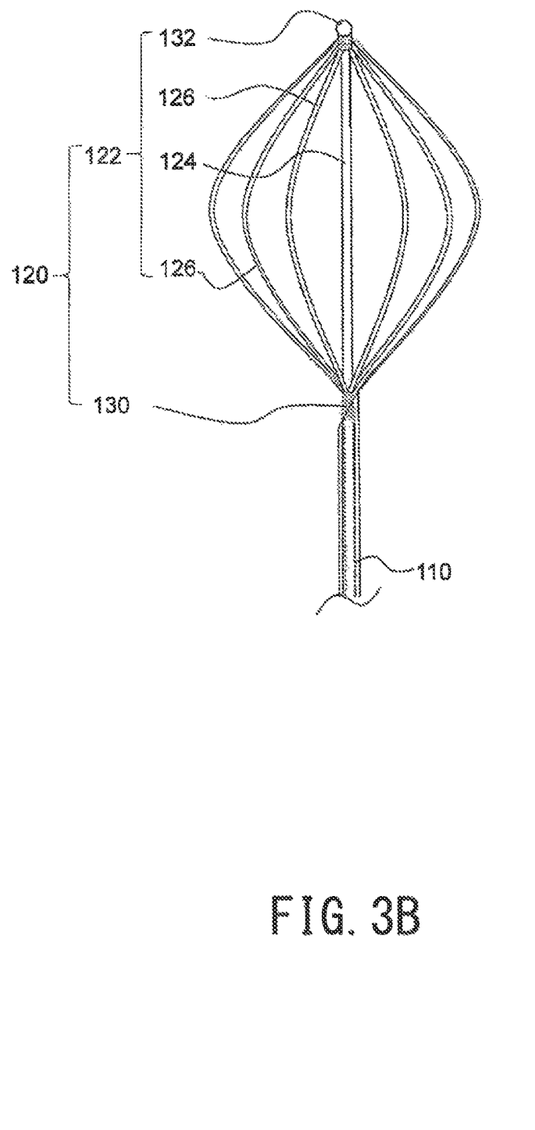
FIG. 3B is a partially cutout cross-sectional view of the distal end portion of the retractor of the present invention showing the developing body extended from the perforation tube and in which the cocoon shape is developed.

FIGS. 3A and 3B are views schematically showing one example of the developing body 120 configuring the retractor of the present invention.

As shown in FIG. 3A, the developing body 120 has the distal end of the movable wire 124 and the distal end of the fixing wire 126 joined at a cap 132 arranged at a tip of the distal end in the excluding section 122. The respective proximal ends of the fixing wires 126 are also fixed with the introducing tube 130, and the movable wire 124 is passed through the introducing tube 130. When the developing body 120 is accommodated in the perforation tube 110, for example, the distal end of the introducing tube 130 is located at the farthest position (i.e., more proximal side in the retractor 100) with respect to the ball shaped cap 132 made from SUS304, and the fixing wire 126 maintains a straightly extended state. Thus, the developing body 120 has a most deformed state in an axial direction of the perforation tube 110, and can freely slide in the perforation tube 110.

As shown in FIG. 3B the developing body 120 can be extended from the perforation tube 110 so that the cocoon-shaped structure can be developed by the plurality of fixing wires 126. In such a state, each distal end of the movable wire 124 and the fixing wire 126 remains fixed to the cap 132, whereas the cap 132 and the distal end of the introducing tube 130 move closer and each fixing wire 126 causes deflection in a direction (radial direction) away from about the axis of the movable wire 124, and the cocoon-shaped structure by the entire plurality of fixing wires 126 can be built as the excluding section 122. The cocoon-shaped structure excludes the inside wall of the hollow organ or the organ in the body cavity, and can form a predetermined space in the hollow cavity or the body cavity.

Figure 4:
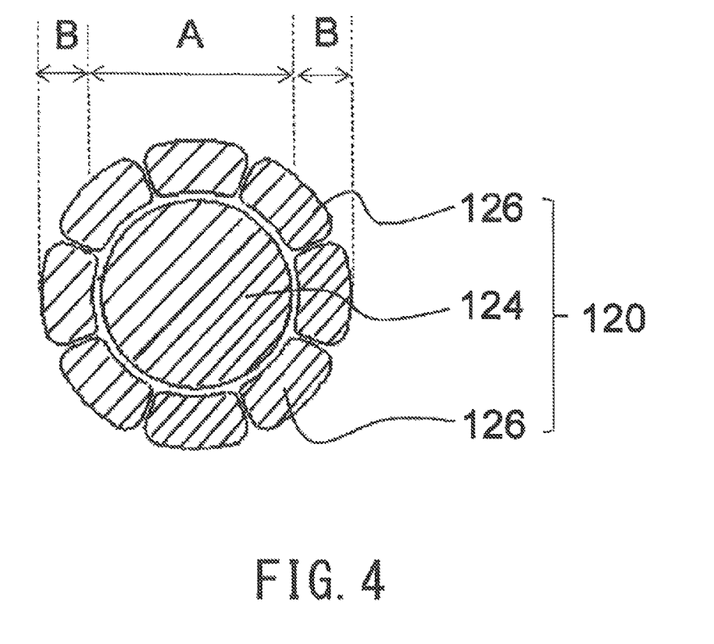
FIG. 4 is a view schematically showing one example of a cross-sectional view (cross-sectional view of movable wire and fixing wire) in a direction orthogonal to a long axis of the developing body configuring the retractor of the present invention.

FIG. 4 is a schematic view showing one example of a cross-sectional view (cross-sectional view of movable wire and fixing wire) in a direction orthogonal to a long axis of the developing body 120 configuring the retractor 100 of the present invention, and is a cross-sectional view of the excluding section 122 of the accommodated (undeveloped) developing body 120.

The diameter A of the movable wire 124 and the thickness B of the fixing wire 126 in FIG. 4 are such that a ratio (A/B) of lengths preferably satisfies, for example two to ten, and preferably three to seven from the standpoint of easiness in the development of the fixing wire 126 and providing sufficient strength to each wire 124, 126. In one embodiment, A is 1.2 mm and B is 0.25 mm (A/B is 4.8).

In FIG. 4, the movable wire 124 configuring the excluding section 122 has a substantially circular cross-section, but is not necessarily limited to such cross-sectional shape. As the force applied when the fixing wire 126 is developed is uniformly dispersed, shapes such as circle, regular polygon (square, regular hexagon, regular octagon, etc.), and the like are preferred. The plurality of fixing wires 126 having substantially the same cross-sectional shape are arranged at the periphery of the movable wire 124. A surface where each fixing wire 126 makes contact with the movable wire 124 preferably has a shape that coincides with the outer diameter of the movable wire 124. This is because the entire capacity of the excluding section 122 during the accommodation can be made as small as possible while avoiding an unnecessary space from being formed between the fixing wire 126 and the movable wire 124.

Figure 5A:
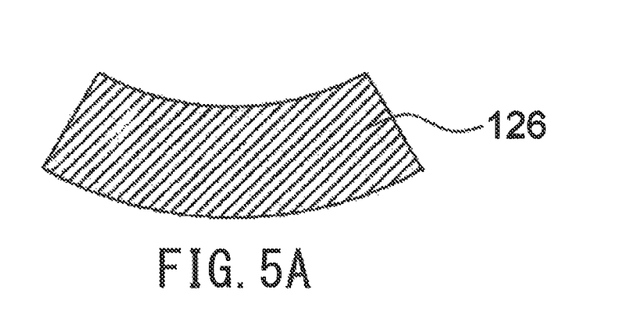
FIGS. 5A to 5C are cross-sectional views of the wire schematically showing an example of a cross-section of a fixing wire of the developing body configuring the present invention.
Figure 5B:
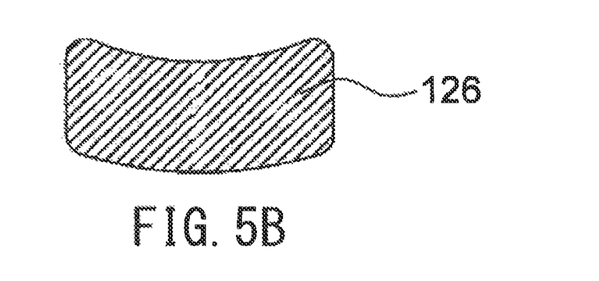
Figure 5C:
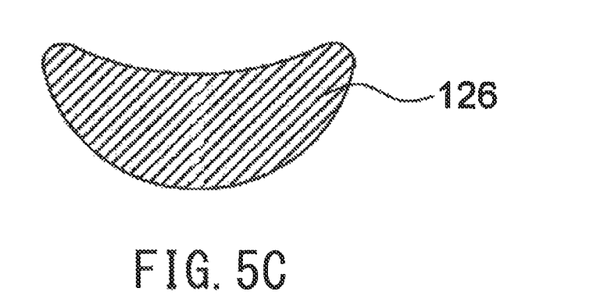

More specifically, the cross-section of the fixing wire 126 has a partial circular ring shape in which a part of the cross-section, as shown in FIGS. 5A to 5C, substantially coincides with a part of the outer periphery of the cross-section of the movable wire 124. In other words, the cross-section of the fixing wire 126 may have a shape as if a part of an arc is cut out as is from the circular ring as shown in FIG. 5A, may have a blunt shape in which four corners in the partial circular ring shape shown in FIG. 5A are rounded to reduce the damage of the surrounding tissues at the time of exclusion as shown in FIG. 5B, or may have a shape in which the respective cross-section is a crescent shape by having a portion corresponding to the outer edge side of the excluding section in the fixing wire 126 to a more rounded blunt shape as shown in FIG. 5C. The cross-section of the plurality of fixing wires 126 is preferably the same with respect to each other to carry out a uniform development.

Figure 6:
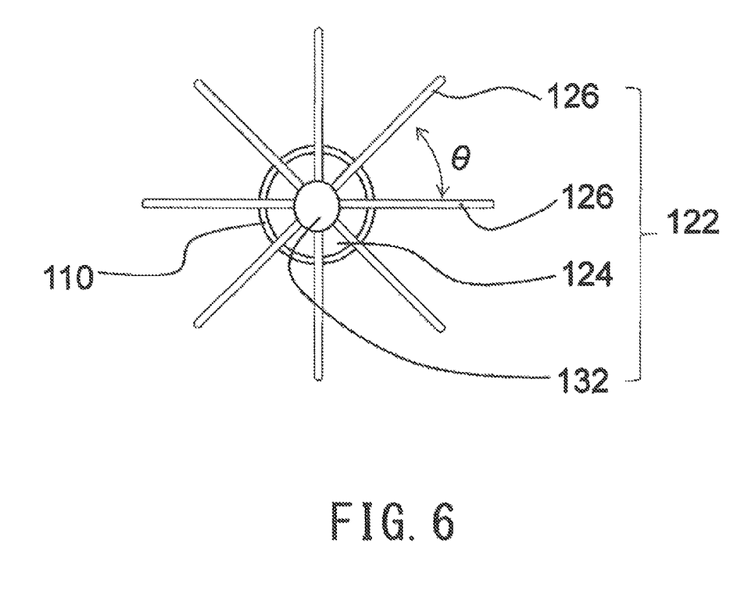
FIG. 6 is a schematic view seen from a distal end side of the retractor when the developing body is extended from the perforation tube and developed in the retractor of the present invention.

FIG. 6 is a schematic view seen from a distal end side of the retractor when the developing body 120 is extended from the perforation tube 110 and developed in the retractor 100 of the present invention.

As shown in FIG. 6, when the developing body 120 is developed, each fixing wire 126 preferably has a substantially equal developing angle (θ) with respect to each other with the movable wire 124 as a center. In other words, the developing angle (θ) can be set by the number of fixing wires 126 configuring the excluding section 122. If each fixing wire 126 is developed at substantially equal developing angle (θ) with respect to each other as shown in FIG. 6, the movable wire 124 can maintain a straight shape in the axial direction without causing warp.

In the retractor 100 of the present invention, the extension of the developing body 120 from the perforation tube 110, the accommodation of the developing body 120 to the perforation tube 110, and the development or the accommodation of the excluding section 122 in the developing body 120 are controlled by the grip 160 provided at the proximal end side of the retractor 100.

Figure 7A:
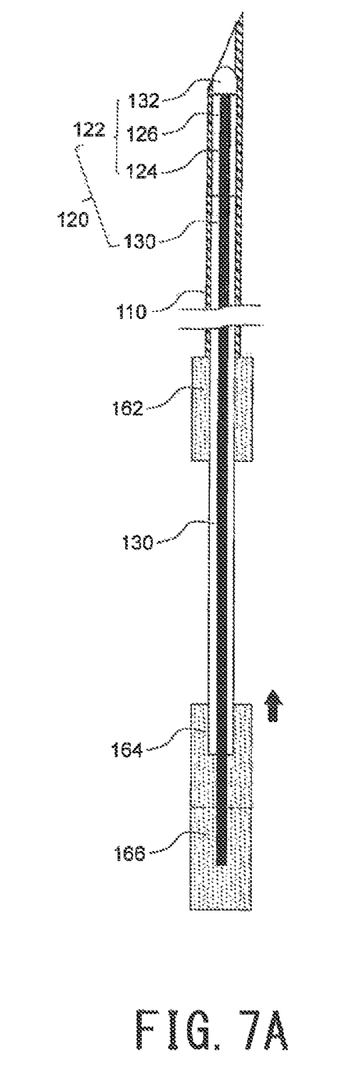
FIG. 7A is a view showing a state in which the first grip portion, and the second grip portion and the third grip portion are separated when the developing body is accommodated in the perforation tube.
Figure 7B:
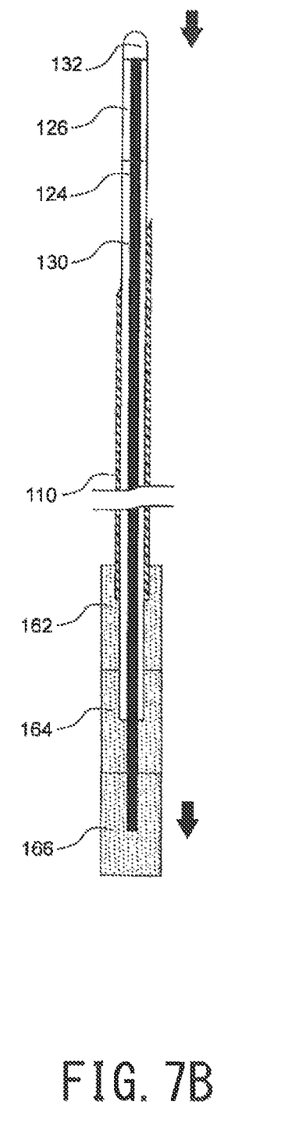
FIG. 7B is a view showing a state in which the developing body is extended from the perforation tube, and the first grip portion and the second grip portion, and the second grip portion and the third grip portion are respectively brought into contact.
Figure 7C:
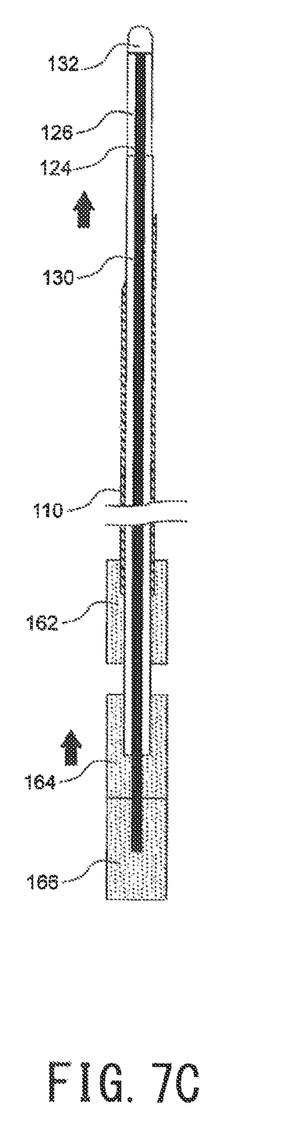
FIG. 7C is a view showing a state in which the developing body is extended from the perforation tube, and the first grip portion, and the second grip portion and the third grip portion are separated.

FIGS. 7A to 7C are schematic cross-sectional views of the retractor showing one example of the retractor 100 of the present invention.

As shown in FIG. 7A, in the present invention, the proximal end of the perforation tube 110 is connected to the first grip portion 162, the proximal end of the introducing tube 130 of the excluding section 122 is connected to the second grip portion 164, and the proximal end of the movable wire 124 of the excluding section 122 is connected to the third grip portion 166. In the retractor 100 of the present invention, when the developing body 120 is accommodated in the perforation tube 110, the first grip portion 162, and the second grip portion 164 and the third grip portion 166 of the grip 160 are separated, as shown in FIG. 7A. In this state, the retractor 100 of the present invention is inserted to the inside wall of the hollow organ or the organ in the body cavity through an incision or by being directly perforated from the tip of the distal end of the perforation tube 110.

Next, the second grip portion 164 and the third grip portion 166 are respectively pushed in toward the distal end side, that is, the first grip portion 162 side with respect to the first grip portion 162. Thus, the introducing tube 130 and the movable wire 124 connected to the second grip portion 164 and the third grip portion 166, respectively, are pushed out toward the distal side, and the developing body 120 is extended from the perforation tube 110.

Thereafter, the development of the fixing wire 126 is carried out from the excluding section 122 in the developing body 120. The development of the fixing wire 126 from the excluding section 122 is carried out, for example, in the following manner according to the respective lengths of the introducing tube 130 and the movable wire 124 with respect to the length of the perforation tube 110, the position relationship of the second grip portion 164 and the third grip portion 166 with respect to the first grip portion 162 when the developing body 120 is extended from the perforation tube 110, and the like.

In other words, as shown in FIG. 7B, when the proximal end of the first grip portion 162 is brought into contact with or is substantially brought into contact with the distal end of the second grip portion 164 under a state the developing body 120 is extended from the perforation tube 110, only the movable wire 124 is sled toward the proximal side with the introducing tube 130 fixed with respect to the perforation tube 110 by pulling out only the third grip portion 166 toward the proximal side (hand side) with respect to the first grip portion 162 and the second grip portion 164. Thus, the distal end of the fixing wire 126 joined with the movable wire 124 at the portion of the cap 132 is also sled toward the proximal side. On the other hand, the proximal end of the fixing wire 126 is joined to the distal end of the introducing tube 130 and is in a fixed state, so that the fixing wire 126 is curved toward the outer side. As a result, the plurality of fixing wires 126 is developed in the excluding section 122, thus expressing the cocoon shape. The cocoon-shaped expression achieves exclusion of the inserted hollow organ or the body cavity.

Alternatively, as shown in FIG. 7(c), when the first grip portion 162 and the second grip portion 164 are separated under a state the developing body 120 is extended from the perforation tube 100, only the introducing tube 130 is sled toward the distal side with respect to the perforation tube 110 and the movable wire 124 by pushing out only the second grip portion 164 toward the distal side with respect to the first grip portion 162 and the third grip portion 166. Thus, only the proximal end of the fixing wire 126 joined to the distal end of the introducing tube 130 is sled toward the distal side and the fixing wire 126 is curved toward the outer side while maintaining the position relationship of the movable wire 124 and the fixing wire 126 at the portion of the cap 132. As a result, the plurality of fixing wires 126 is developed in the excluding section 122, and a cocoon-shaped structure is expressed. The cocoon-shaped expression achieves the exclusion of the inserted hollow organ or the body cavity.

In FIGS. 7B and 7C, the length of pulling out or pushing out the third grip portion 166 and/or second grip portion 164 is fluctuated, so that the size of the cocoon-shaped structure expressed in the excluding section 122 can be freely changed.

The retractor of the present invention is used to carry out exclusion in various surgeries in the hollow organs such as stomach, small intestine, large intestine, and vagina as well as the other organs such as liver, pancreas, kidney, gallbladder, spleen, uterus, lungs, and the like.

For example, in the surgery of stomach and esophagus, the retractor of the present invention is inserted to the lower surface of the hepatic left lobe interfering with the operative field to elevate it toward the abdominal side, so that the surgery can be proceeded more safely and efficiently without the interference to the operative field. Similarly, in the operation at the pelvic floor, the surgical operation of the periphery of the rectum can be efficiently carried out by spreading the uterus using the retractor of the present invention.

INDUSTRIAL APPLICABILITY

According to the present invention, a retractor that can freely exclude the organ can be provided. Furthermore, according to the present invention, the retractor is also useful in that gas-less surgery can be carried out, for example, as the field of view and the operation space can be ensured without injecting gas into the body cavity.

REFERENCE SIGNS LIST 100 retractor
110 perforation tube
120 developing body
122 excluding section
124 movable wire
126 fixing wire
130 introducing tube
132 cap
160 grip
162 first grip portion
164 second grip portion
166 third grip portion

The invention claimed is:

1. A retractor for excluding an inside wall of a hollow organ or an organ in a body cavity, the retractor comprising:
   a rigid perforation tube having a tip at a distal end;
   a developing body that is configured to be accommodated and extended with respect to the distal end of the perforation tube; and
   a grip connected to respective proximal ends of the perforation tube and the developing body, wherein the developing body includes:
      an excluding section configured by a movable wire and a plurality of fixing wires arranged at a periphery of the movable wire, and
      an introducing tube extended from the excluding section, the movable wire being passed through the introducing tube; wherein:
   a distal end of the movable wire and distal ends of the fixing wires are joined in the excluding section, and
   the grip includes, in order from a distal end of the grip, a first grip portion, a second grip portion, and a third grip portion, wherein the excluding section is caused to extend from the tip of the perforation tube by moving the second grip portion and the third grip portion toward the first grip portion in a state where the excluding section is closed and accommodated in the perforation tube, and the excluding section is capable of being developed, by moving the third grip portion toward the distal end of the grip without moving the second grip portion in a state where the excluding section is closed and extended from the tip of the perforation tube.

2. The retractor according to claim 1, wherein the perforation tube is a straight tube.

3. The retractor according to claim 1, wherein a cross-section of the movable wire has a substantially circular shape.

4. The retractor according to claim 3, wherein a cross-section of each fixing wire has a partial circular ring shape in which a part of the cross-section substantially coincides with one part of an outer periphery of the cross-section of the movable wire.

* * * * *